United States Patent [19]

Okawara et al.

[11] 4,328,170
[45] May 4, 1982

[54] PROCESS FOR PREPARING AN α-CYANOACRYLATE

[75] Inventors: Makoto Okawara, Tokyo; Yukihisa Takaoka, Ushiku; Makoto Kameyama, Chiba; Iwakichi Sugiyama, Narashino, all of Japan

[73] Assignee: Matsumoto Seiyaku Kogyo Kabushiki Kaisha, Ichikawa, Japan

[21] Appl. No.: 87,970

[22] Filed: Oct. 25, 1979

[30] Foreign Application Priority Data

Nov. 2, 1978 [JP] Japan ................................. 53-134602
Sep. 12, 1979 [JP] Japan ................................. 54-116166

[51] Int. Cl.$^3$ .................. C07C 120/00; C07C 121/30; C07C 121/46; C07C 121/52
[52] U.S. Cl. ................................ 260/465.4; 260/464; 260/465 D
[58] Field of Search ................ 260/465.4, 465 D, 464

[56] References Cited

U.S. PATENT DOCUMENTS

| | | | |
|---|---|---|---|
| 2,721,858 | 10/1955 | Joyner et al. | 260/465.4 X |
| 2,912,454 | 11/1954 | McKeever | 260/465.4 |
| 2,926,188 | 2/1960 | McKeever et al. | 260/465.4 |
| 3,254,111 | 5/1966 | Hawkins et al. | 260/465.4 |
| 3,465,027 | 9/1969 | Hawkins | 260/465.4 X |
| 3,992,432 | 11/1976 | Napier et al. | 260/604 HF X |
| 3,996,259 | 12/1976 | Lee et al. | 260/465.1 X |
| 4,079,075 | 3/1978 | Lee et al. | 260/465.1 X |
| 4,174,347 | 11/1979 | Austermuhle-Bertola | 260/465.4 |

FOREIGN PATENT DOCUMENTS

| | | | |
|---|---|---|---|
| 1227144 | 4/1971 | United Kingdom | 260/465.1 |
| 1324763 | 7/1973 | United Kingdom | 260/465.1 |

*Primary Examiner*—Joseph Paul Brust
*Attorney, Agent, or Firm*—Martin Smolowitz

[57] ABSTRACT

A process for producing an α-cyanoacrylate which comprises reacting a cyanoacetate with formaldehyde in the presence of a catalyst and a solvent, wherein a compound having phase transfer catalytic activity is used as the catalyst.

8 Claims, 1 Drawing Figure

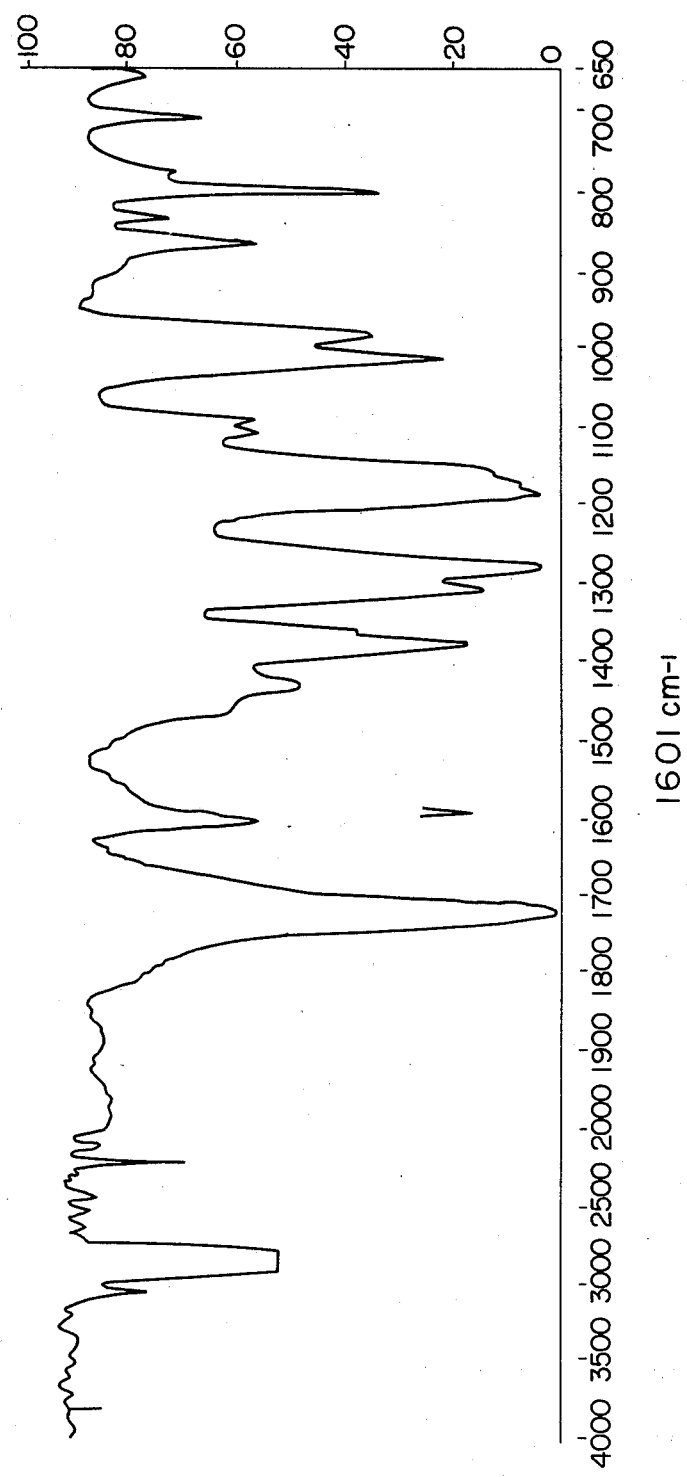

PROCESS FOR PREPARING AN ALPHA-CYANOACRYLATE

BACKGROUND OF THE INVENTION

The present invention relates generally to processes for preparing α-cyanoacrylates. In particular, the present invention relates to a process for reacting a cyanoacetate with formaldehyde in the presence of a compound having phase transfer catalytic activity (hereinafter sometimes referred to as phase transfer catalyst) as a catalyst.

Various processes for preparing α-cyanoacrylate monomers which are widely known as base material for instantaneous adhesives have been proposed.

It is well known that processes for preparing α-cyanoacrylate monomers which have been generally practiced are based on and are improvements of a process disclosed in, for example, U.S. Pat. No. 2,467,926, which issued to A. E. Ardis. A typical one of these processes comprises reacting paraformaldehyde with a cyanoacetate in a medium of methanol in the presence of piperidine as a catalyst and thereafter removing the methanol from the reaction mixture. Then, a dehydrating solvent is added to the reaction mixture to azeotropically dehydrate the mixture, and phosphorus pentoxide is added to the resulting α-cyanoacrylate polymer (addition and condensation polymer between cyanoacetate and formaldehyde (hereinafter simply referred to as polymer) to depolymerize it, thereby producing α-cyanoacrylate monomers.

The above described process has been generally practiced, and piperidine is considered to be an effective catalyst particularly for activating formalin and a cyanoacetate.

This process includes addition and condensation polymerization, dehydration, and depolymerization steps. These steps are ordinarily carried out in one pot operation. Since the intermediate product is supplied to the subsequent step without being isolated and purified, contamination of the final product with impurities must be carefully avoided. The piperidine used in the typical reaction as described above is an essential component for the addition and condensation step, but it is an unnecessary component in the subsequent steps. When the piperidine remains in the subsequent steps, it may have an adverse effect on the dehydration and depolymerization steps. Although most of the piperidine is distilled off during the removal of methanol by distillation, the remaining piperidine is generally brought into the depolymerization step. This piperidine interferes with the depolymerization reaction and also results in a remarkable reduction in the quality and stability of the resulting crude monomer. In order to avoid these disadvantages, washing prior to the dehydration step or addition of various acids after the dehydration step has been proposed. However, these measures provided no satisfactory result.

We have previously found that when a cyanoacetate is reacted with formaldehyde in a medium of water or an organic solvent in the presence of an alkali metal hydroxide or a basic ion-exchange resin as a catalyst, good results are obtained. This process produces α-cyanoacrylate monomers of very good quality in a high yield, as compared with the conventional process using an amine or an amine-NaOH mixed catalyst in a methanol solvent. However, because in this process water is employed, the dehydration operation must be carefully conducted, which makes the operation complicated.

Hitherto, in reacting a cyanoacetate with formaldehyde, an amine such as piperidine has been generally used. Piperidine is one of the most favourable amine catalysts. However, the piperidine is not always the most effective for activating the formaldehyde or cyanoacetate from view point of a basicity. For this reason, a relatively long period of time of reaction and heating under reflux has been required, which have caused some side reactions. In addition, because in the conventional process for preparing an α-cyanoacrylate, the addition and condensation, the dehydration and the depolymerization are carried out in one pot operation and the products resulting from the respective steps are not purified, it is estimated that the catalyst or the material originating in the catalyst may cause an unfavourable behavior in the product.

In this connection, when the process we have previously discovered is carried out, the catalyst may be easily treated by washing and filtration or formation of a salt, whereby the catalyst is prevented from adversely affecting the product. In addition, because the addition and condensation can be carried out under a relatively mild condition, little side reaction occurs. However, by this process, it is difficult to conduct rapid dehydration of the polymer.

We have since conducted various experiments to overcome this difficulty and to develop improved conditions. As a result, we have found that the use of a phase transfer catalyst is very effective.

SUMMARY OF THE INVENTION

The present invention provides a process for preparing an α-cyanoacrylate which comprises reacting a cyanoacetate with formaldehyde in the presence of a catalyst and a solvent, wherein the catalyst is a combination of an onium compound, macrocyclic polyether, or nonionic surface active agent with an alkaline compound, and the solvent is a mixture of water and organic solvent.

BRIEF DESCRIPTION OF THE DRAWING

The single FIGURE in the drawing shows the infrared absorption spectrum of ethyl-α-cyanoacrylate.

DETAILED DESCRIPTION OF THE INVENTION

The cyanoacetate used in the present invention is represented by the formula $$NCCH_2COOR \quad (I)$$

wherein R represents (1) an alkyl having 1 to 10 carbon atoms optionally substituted by a lower alkoxy, halogen or phenyl; (2) cyclohexyl; and (3) aryl optionally substituted by a halogen. Examples of the alkyl are methyl, ethyl, i-propyl, n-propyl, n-butyl, t-butyl, n-amyl, i-amyl, t-amyl, n-hexyl, 2-ethylhexyl, n-octyl, decyl, methoxyethyl, ethoxyethyl, ethoxybutyl, chloroethyl, and benzyl, and examples of the aryl are phenyl and chlorophenyl. The formaldehyde used in the present invention is any of those which are generally used, such as paraformaldehyde and formalin.

A suitable molar ratio of the cyanoacetate to the formaldehyde in the practice of the reaction is equal to or approximately 1:1.

In accordance with the present invention, a compound having phase transfer catalytic activity is used as a catalyst in the reaction of the cyanoacetate and the formaldehyde. For this catalyst, use is made of a compound capable of promoting the reaction occurring in a two-phase system. However, we do not wish the present invention to be limited by reaction mechanism. Examples of such a compound are onium compounds, macrocyclic polyethers and nonionic surface active agents. Macrocyclic aminopolyethers and phosphoryl compounds may also be used as the compound.

These compounds are used in combination with an alkali compound, e.g., a hydroxide of Li, Na, K, Rb or Cs. The phase transfer catalyst may also be previously treated with these alkalis. Also, the alkali metal carbonate such as sodium carbonate, sodium bicarbonate, potassium carbonate and potassium bicarbonate, and alkaline earth metal hydroxide such as calcium hydroxide, barium hydroxide and magnesium hydroxide, and an alkaline earth metal carbonate such as calcium carbonate, calcium bicarbonate, magnesium carbonate and magnesium bicarbonate may be used. These alkali compounds may be used singly or in combination with each other.

The above mentioned alkali metal hydroxide and alkaline earth metal hydroxide include an alkali metal oxide such as sodium oxide, an alkaline earth metal oxide such as calcium oxide and an alcoholate, e.g., sodium methylate and calcium methylate, which is capable of dissolving in water to form an alkali metal hydroxide or alkaline earth metal hydroxide. The use of such other alkali compounds falls within the scope of the present invention.

One example of the onium compounds is a quaternary onium salt represented by the formula

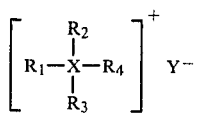 (II)

wherein: X represents a nitrogen or phosphorus atom; each of $R_1$, $R_2$, $R_3$ and $R_4$ represents a hydrocarbon group having from 1 to 22 carbon atoms such as alkyl, aralkyl and aryl; and $Y^-$ represents a monovalent anion such as $Cl^-$, $Br^-$, $I^-$ and $HSO_4^-$.

The onium compound as represented by the above formula is generally an ammonium compound or phosphonium compound which is used in the form of a halide such as a chloride, bromide, or iodide, a hydrogensulfate or an alkyl sulfate such as methyl sulfate or ethyl sulfate.

Another onium salt is a sulfonium compound represented by the formula

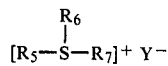 (III)

wherein: each of $R_5$, $R_6$ and $R_7$ represents an alkyl group having from 1 to 18 carbon atoms; and $Y^-$ represents a monovalent anion. This compound may be used in the form of a halide such as a chloride, bromide, or iodide or an alkyl sulfate salt such as methyl sulfate or ethyl sulfate.

Examples of such onium compounds are tetra-n-butyl ammonium chloride, tetra-n-butyl ammonium bromide, tetra-n-butyl ammonium iodide, trimethyl benzyl ammonium chloride, trimethyl benzyl ammonium bromide, triethyl benzyl ammonium chloride, triethyl benzyl ammonium bromide, methyltrioctyl ammonium chloride, trimethyloctyl ammonium bromide, tricaprylmethyl ammonium chloride, triphenylmethyl ammonium chloride, methyl-2-methylphenyl ammonium chloride, triethylpalmityl ammonium chloride, trimethylpalmityl ammonium chloride, triethylstearyl ammonium chloride, trimethylbehenyl ammonium chloride, tetramethyl phosphonium iodide, tetra-n-butyl phosphonium bromide, tetraphenyl phosphonium bromide, triethyloctyl phosphonium bromide, triethylpalmityl phosphonium bromide, tetrabutyl ammonium hydrogensulfate, triethylbenzyl ammonium hydrogensulfate, tetrabutyl ammonium ethyl sulfate, triethylbenzyl ammonium methyl sulfate, ethyl-2-methylpentyl-2-methylundecyl sulfonium ethyl sulfate, and methyldinonyl sulfonium methyl sulfate.

As clear from the above, these onium compounds may be ordinarily used in combination with an alkali compound selected from the group consisting of alkali metal hydroxide, alkali metal carbonate, alkaline earth metal hydroxide, alkaline earth metal carbonate and mixture thereof. They may also be used in the form of an onium hydroxide prepared by previously reacting them with said alkali compound. Also, these onium compounds may be used in the form of a basic ion-exchange resin prepared by substituting a high polymer skeleton for the alkyl moiety of the compounds. As the high polymer skeleton, polystyrene resins such as styrene-divinylbenzene copolymer are generally used. As the functional group, a quaternary ammonium or phosphonium group is generally used. Such strongly basic anion exchange resin is commercially available under the trade name of Duolite A-101-D, A-102-D, ES-111, Dowex 11, 2, 21K, Amberlite IRA-400, IRA401, 900, 402, IRA911.

Other examples of the phase transfer catalyst which may be used in the present invention are macrocyclic polyethers which are also called crown ethers, such as 1, 4, 7, 10, 13, 16-hexaoxacyclooctadecane (which is ordinarily called 18-crown-6, wherein the number 18 represents the total number of the atoms constituting the ring and the number 6 represents the number of oxygen atoms among the above mentioned atoms), 3, 4-benzo-1, 6, 9, 12, 15, 18, 21-heptaoxacyclotricos-3-ene, similar macrocyclic aminoethers such as [2.2.2.] cryptate and phosphoryl compounds such as 2-phosphoryl sulfoxide. Surface active agents are also useful. Particularly, nonionic surface active agents are preferable. Polyalkylene oxide ethers wherein the alkylene oxide is from 1 to 50 units, usually from 5 to 10 units and the ether group has from about 8 to 20 carbon atoms are generally used. Macrocyclic ethers and nonionic surface active agents may also be used in combination with the abovementioned alkali compound.

In the case where the reaction is carried out by using such a phase transfer catalyst, it is preferably that the reaction be carried out in a medium of water, an organic solvent which is nonreactive to an alkali material, or a mixture of water and an organic solvent. Examples of the organic solvent are hydrocarbons or their derivatives such as cyclohexane, benzene, xylene, methylene chloride, chlorobenzene and dichlorobenzene and ethers such as di-n-butyl ether, diisoamyl ether, diphenyl ether and tetrahydrofuran. By using these organic solvents singly or in mixtures of the two or more thereof, desirable results are obtained.

The reaction of the cyanoacetate represented by the formula (I) with the paraformaldehyde can be carried out by charging 50 to 300 parts of water and 50 to 300 parts of an organic solvent, respectively, per mole of a cyanoacetate, into a reaction vessel equipped with a stirrer, and adding 0.01 to 5 parts, preferably 0.05 to 4 parts of a phase transfer catalyst, e.g., a quaternary ammonium salt, and 0.01 to 10 parts, preferably 0.02 to 8 parts of an alkali metal hydroxide or an alkaline earth metal hydroxide or a compound capable of forming an alkali metal hydroxide or an alkaline earth metal hydroxide on dissolving in water or an alkali metal carbonate or an alkaline earth metal carbonate which is taken singly or in mixture with each other, into the reaction vessel and dissolving these compounds homogeneously in the solvent while stirring the contents of the vessel. In the case where the phase transfer catalyst is added in a quantity less than 0.01 part, the rate of reaction is too slow. The addition of this catalyst in a quantity greater than 5 parts results in no significant additional effect. Furthermore, in the case where the alkali or alkaline earth metal compound is added in a quantity less than 0.01 part, the rate of reaction is too slow. On the other hand, the addition of this compound in a quantity greater than 10 parts provides an excessively high alkalinity and may cause side-reactions.

Then, 1 mole of paraformaldehyde is suspended in the reaction solution and, if necessary, the suspension is heated to a temperature of 30° to 40° C. Thereafter, 1 mole of a cyanoacetate is added dropwise into the suspension. After the addition of the cyanoacetate, the reaction mixture is stirred at room temperature for 10 to 60 minutes and then heated to a temperature of 60° to 80° C. for 5 to 30 minutes, and, at the end of that time, the reaction mixture is cooled to cease the reaction.

If desired, an acid such as hydrochloric acid, sulfuric acid, nitric acid or p-toluene sulfonic acid is added to the reaction mixture, stirred and allowed to stand to separate the mixture into an aqueous phase and a polymer solution phase. After the aqueous phase is removed, a polymer solution is obtained. The polymer solution is distilled under atmospheric pressure to azeotropically remove the remaining water. After the dehydration treatment has been completed, the resulting solution is further distilled under atmospheric pressure or reduced pressure to remove the remaining organic solvent completely thereby to obtain a polymer. In accordance with the process of the present invention, the dehydration treatment can be very easily carried out, and the resulting polymer is a colorless or light yellow viscous liquid. When the ion-exchange resin is used as the phase transfer catalyst, after the addition reaction has been completed, the reaction mixture may be filtered to recover the ion-exchange resin, and, subsequently, the same procedure may be followed.

In the case where the conventional phase transfer catalyst such as the above mentioned onium compounds and nonionic surface active agent is used, water and an organic solvent immiscible with water may be used as the solvent. However, when a phase transfer catalyst having no electric charge, such as macrocyclic polyether and macrocyclic aminoether, is used, water may be omitted or remarkably reduced.

The resultant polymer to which $P_2O_5$, hydroquinone or a plasticizer is added, as required, is depolymerized in a stream of gaseous sulfur dioxide at a solution temperature of 170° to 210° C. under reduced pressure of several millimeters of Hg to give an α-cyanoacrylate monomer. The yield of the crude monomer is 85% or more based on the weight of the cyanoacetate. When the crude monomer is stored in a sealed container under atmospheric pressure for a long period of time of a half year or longer, no change in viscosity occurs. The crude monomer thus prepared is highly pure, and, thus, it can be easily purified to obtain an α-cyanoacrylate monomer of good quality. The purified monomer is useful as a base for an instantaneous adhesive or other materials.

One of the outstanding features of the process according to the present invention is that the reaction of the cyanoacetate with the formaldehyde can be carried out at room temperature or a relatively low temperature for a short period of time and as a result, the occurrence of side-reactions can be remarkably suppressed. Another feature is that the impurity content of the polymer product is very low, and the dehydration treatment can be easily carried out because the used catalyst can be removed outside of the system by washing treatment or filtration separation. As a result, the depolymerization of the resultant polymer can be easily carried out, and the resulting crude monomer is of high purity, which results in a purified monomer of high quality. This is also one advantageous feature of the present invention.

In order to indicate more fully the nature and utility of this invention, the following specific examples of practice are set forth, it being understood that these examples are presented as illustrative only and that they are not intended to limit the scope of the invention. In the following examples, all quantities expressed in parts are by weight.

EXAMPLE 1

100 parts of water and 150 parts of toluene were charged into a reaction vessel, and 3 parts of sodium hydroxide and 0.3 part of triethylbenzyl ammonium chloride were then dissolved in the mixture of the vessel. Thereafter, 31 parts of paraformaldehyde was added to the vessel and the resultant mixture was heated to a temperature of 30° C. with stirring.

Then, 113 parts of ethyl cyanoacetate was added to the mixture in about 20 minutes while the mixture was stirred, and the resultant mixture was reacted together at room temperature for 20 minutes. At the end of that time, the reaction mixture was heated at a temperature of 80° C. for 15 minutes. After completion of the heating period, the reaction mixture was cooled.

100 ml of 1-N sulfuric acid was added to the cooled reaction mixture, and the mixture was stirred for 10 minutes. Thereafter, the reaction mixture was allowed to stand to separate it into an aqueous phase and a polymer-containing-phase. After the aqueous phase was removed, the resulting polymer-toluene solution was distilled under atmospheric pressure to remove the remaining water as an azeotropic mixture with toluene. Upon completion of the dehydration, the resulting solution was distilled under atmospheric pressure and reduced pressure to completely remove the remaining toluene. A polymer in the form of a light yellow viscous liquid was obtained.

4 parts of $P_2O_5$ and 0.6 part of hydroquinone were added to this liquid polymer. The resulting liquid was depolymerized in a stream of gaseous sulfur dioxide under reduced pressure of 5 mmHg. As a result, 112 parts of a crude monomer distilled out at a liquid temperature of 170° to 205° C. was obtained. The yield of the crude monomer was 89.6% based on the weight of the cyanoacetate (the yields set forth hereinafter are on the same basis).

1 part of $P_2O_5$ and 0.6 part of hydroquinone were added to 100 parts of the crude monomer. The resulting mixture was distilled in a stream of aqueous sulfur dioxide under reduced pressure. 91 parts of a fraction distilled out at a temperature of 65° to 67° C. under a pressure of 6 mmHg was obtained. The fraction was colorless and clear and exhibited an infrared absorption spectrum as shown in the accompanying drawing. In view of the infrared absorption spectrum in combination with the result of gas chromatography analysis, the fraction was confirmed to be ethyl-α-cyanoacrylate. The purified monomer was of high purity and suitable as a base for instantaneous adhesives. When the crude monomer was stored in a sealed state, no change in viscosity was observed for over a half year and its stability in storage was excellent.

EXAMPLE 2

The procedural steps as described in Example 1 were repeated except that 0.3 part of tetrabutyl ammonium bromide was used instead of the triethyl benzyl ammonium chloride, and 180 parts of isoamyl ether was used instead of the toluene. As a result, a light yellow, viscous liquid polymer was obtained. When the liquid polymer was depolymerized in a stream of gaseous sulfur dioxide under reduced pressure, 115 parts of a crude monomer distilled out at a temperature of 175° to 210° C. under reduced pressure of 8 mmHg was obtained in a yield of 92%.

1.5 parts of $P_2O_5$ and 0.6 part of hydroquinone were added to 100 parts of the crude monomer. The resulting mixture was distilled in a stream of gaseous sulfur dioxide under reduced pressure. 91 parts of a fraction distilled out at a temperature of 66° to 68° C. under a pressure of 7 mmHg was obtained.

The fraction was colorless and clear. Analysis of this fraction indicated that it was ethyl-α-cyanoacrylate.

EXAMPLE 3

The procedure as described in Example 1 was repeated except that 0.4 part of tetraphenyl phosphonium chloride was used instead of the triethylbenzyl ammonium chloride. As a result, a light yellow, viscous liquid polymer was obtained. The liquid polymer was depolymerized in the same manner as described in Example 1. 110 parts of a crude monomer distilled out at a liquid temperature of 170° to 205° C. under reduced pressure of 6 mmHg was obtained in a yield of 86.6%. 100 parts of the resulting crude monomer was purified by the distillation described in Example 1. 90.5 parts of a fraction distilled out at a temperature of 63° to 65° C. under a pressure of 5 mmHg was obtained. The fraction was colorless and clear. Analysis of this fraction by infrared absorption spectrum and gas chromatography indicated that it was ethyl-α-cyanoacrylate.

EXAMPLE 4

The same procedure as described in Example 2 was repeated except that 127 parts of isopropyl cyanoacetate was used instead of the ethyl cyanoacetate, and 100 ml of a 1-N solution of p-toluene sulfonic acid was used instead of sulfuric acid. As a result, a light yellow liquid polymer was obtained. When the polymer was depolymerized, 116.9 parts of a crude monomer distilled out at a liquid temperature of 175° to 230° C. under a pressure of 6 mmHg was obtained in a yield of 85.3%.

When 100 parts of the crude monomer was purified in the manner described in Example 2, 87 parts of a fraction distilled out at a temperature of 67° to 70° C. under a pressure of 6 mmHg was obtained.

Analysis of this fraction by infrared absorption spectrum and gas chromatography indicated that it was isopropyl-α-cyanoacrylate.

EXAMPLE 5

The procedure described in Example 1 was followed except that triethyloctyl ammonium hydrogen sulfate was used instead of triethylbenzyl ammonium chloride. As a result, 107 parts of a crude monomer distilled out at a liquid temperature of 170° to 205° C. under a reduced pressure of 6 mmHg was obtained in a yield of 85.6%.

When 100 parts of the monomer was purified in the manner described in Example 1, 89 parts of a colorless clear fraction was obtained. Analysis of this fraction by infrared absorption spectrum and gas chromatography indicated that it was ethyl-α-cyanoacrylate.

EXAMPLE 6

100 parts of water and 200 parts of benzene were charged into a reaction vessel and potassium hydroxide was then dissolved thereinto. Further, 8 parts of a strongly basic ion-exchange resin (of a trade name: Amberlite IRA400) was suspended in the resulting solution. 31 parts of paraformaldehyde was added to the suspension, and 113 parts of ethyl cyanoacetate was then added dropwise thereto in 20 minutes while the mixture was stirred. The resulting mixture was stirred for another period of 20 minutes. Thereafter, the mixture was heated at a temperature of 70° C. for 15 minutes to complete the reaction. Thereafter, the reaction mixture was cooled to room temperature.

The reaction mixture was then filtered through a glass filter to remove the ion-exchange resin. The ion-exchange resin remaining on the filter was washed with 50 ml of benzene. The filtrate combined with the wash was distilled at room temperature to carry out azeotropic dehydration. After the dehydration treatment was completed, the resulting liquid was distilled under atmospheric pressure and reduced pressure to completely remove the benzene. A substantially colorless, clear, viscous liquid polymer was obtained. 1.5 parts of $P_2O_5$ and 0.6 part of hydroquinone were added to this polymer. Then, the polymer was depolymerized in a stream of gaseous sulfur dioxide under reduced pressure. 112 parts of a crude monomer distilled out at a liquid temperature of 170° to 208° C. under a pressure of 7 mmHg was obtained in a yield of 89.6%.

1 part of $P_2O_5$ and 0.6 part of hydroquinone were added to 100 parts of the crude monomer. Then, the crude monomer was purified in a stream of gaseous sulfur dioxide. 90.5 parts of a fraction distilled out at a temperature of 64° to 66° C. under a pressure of 5 mmHg was obtained.

This fraction was colorless and clear. Analysis of this fraction indicated that it was ethyl-α-cyanoacrylate.

EXAMPLE 7

100 parts of water and 180 parts of benzene were charged into a reaction vessel, and 2.5 parts of lithium hydroxide (LiOH) was dissolved thereinto. Then, 3 parts of a nonionic surface active agent, polyethylene oxide nonyl phenol ether (n=10), commercially available under the trade name of Noniolite PN10, manufactured by Kyōeisha Yushi Kagaku Kōgyō K.K., Japan, was added to the above solution and the resulting mixture was stirred. 113 parts of ethyl cyanoacetate was then added dropwise to the mixture over 20 minutes to start the polymerization reaction. The reaction mixture was stirred at room temperature for 20 minutes and thereafter, heated at 60° to 70° C. for 10 minutes to complete the reaction.

The reaction mixture was cooled to room temperature and washed with water. After the washing operation, 100 ml of 1-N p-toluene sulfonic acid was added to the mixture, and the resulting mixture was allowed to stand thereby to separate it into an aqueous phase and a polymer-benzene phase. After the aqueous phase was removed, the polymer-benzene phase was distilled to carry out azeotropic dehydration. After the dehydration treatment, the benzene remaining in the polymer phase was completely distilled off under atmospheric pressure and reduced pressure. A substantially colorless viscous liquid polymer was obtained.

The liquid polymer to which 2 parts of $P_2O_5$ and 0.6 part of hydroquinone had been added was depolymerized in a stream of gaseous sulfur dioxide. 108 parts of a fraction distilled out at a liquid temperature of 170° to 205° C. under a reduced pressure of 6 mmHg was obtained in a yield of 86.4%.

100 parts of the crude monomer was purified in the manner described in Example 1. 90.5 parts of a fraction distilled out at a temperature of 66° to 68° C. under a pressure of 6 mmHg was obtained. This fraction was colorless and clear. Analysis of this fraction indicated that it was ethyl-α-cyanoacrylate.

EXAMPLE 8

250 parts of toluene was charged into a reaction vessel, to which 3 parts of KOH and 6 parts of 18-crown-6 were then added. 31 parts of paraformaldehyde was further added to the vessel. The resulting mixture was stirred at a temperature of 30° C. for 30 minutes.

113 parts of ethyl cyanoacetate were added during about 20 minutes to the mixture while it was stirred. The resulting mixture was polymerized for 20 minutes and was then heated to a temperature of 80° C. at which it was maintained for 15 minutes to complete the reaction.

100 parts of 1-N HCl was added to the reaction mixture and the resulting mixture was stirred for 10 minutes. After an aqueous phase was separated from the mixture, a solution of a polymer in toluene was obtained. The solution was distilled under atmospheric pressure to carry out azeotropic dehydration. The polymer solution from which a substantial quantity of toluene was removed was added to 1,000 parts of ethyl ether, and the resulting mixture was stirred and then allowed to stand thereby to precipitate a polymer.

The resulting polymer phase was placed in a flask and subjected to distillation under reduced pressure to remove the ethyl ether and the toluene, whereupon 90 parts of a polymer was obtained. 1.5 parts of $P_2O_5$ and 0.4 part of hydroquinone were added to the polymer, which was depolymerized in a stream of gaseous sulfur dioxide under a reduced pressure of 5 mmHg. 84 parts of a crude monomer distilled out at a liquid temperature of 165° to 200° C. was obtained in a yield of 93% with respect to the polymer.

To 80 parts of the crude monomer, 0.8 part of $P_2O_5$ and 0.3 part of hydroquinone were added, and the resulting mixture was distilled in a stream of gaseous sulfur dioxide under reduced pressure. 72 parts of a fraction distilled out at a temperature of 65° to 67° C. under a pressure of 6 mmHg was obtained.

Analysis of this fraction indicated that it was ethyl-α-cyanoacrylate.

EXAMPLE 9

120 parts of water and 150 parts of toluene were charged into a reaction vessel. Then, 6 parts of $Na_2CO_3$ and 0.5 part of tributylbenzyl ammonium chloride were dissolved in the solvents contained in the vessel. 31 parts of paraformaldehyde was further added to the solution. The resulting mixture was stirred and heated to a temperature of 30° C.

113 parts of ethyl cyanoacetate was added to the mixture over about 20 minutes while the mixture was stirred. After this addition, the resulting mixture was maintained at a temperature of 30° C. for 20 minutes to cause reaction of the mixture. At the end of that time, the reaction mixture was further reacted at a temperature of 80° to 85° C. for 30 minutes to complete the reaction. The reaction mixture was cooled and allowed to stand thereby to separate it into an aqueous phase and a polymer-toluene phase. After the aqueous phase was removed, the polymer-toluene phase was further washed two times with portions of 150 parts of water, and the aqueous phase was separated from the polymer-toluene phase. A light yellow clear polymer-toluene solution was obtained.

The polymer-toluene solution was distilled at atmospheric pressure to carry out azeotropic dehydration. After the dehydration operation, the remaining toluene was distilled off under atmospheric pressure and then reduced pressure. A light yellow viscous liquid polymer was obtained. 4 parts of $P_2O_5$ and 0.7 part of hydroquinone were added to the polymer, which was depolymerized in a stream of gaseous sulfur dioxide under a reduced pressure of 5 mmHg. 113 parts of a crude monomer distilled out at a temperature of 170° to 215° C. was obtained. During the depolymerization reaction, no side reaction such as formation of crystalline materials was observed.

The yield of the crude monomer was 90% with respect to the cyanoacetate ester.

To 100 parts of the crude monomer 1, part of $P_2O_5$ and 0.5 part of hydroquinone were added, and the resulting mixture was distilled in a stream of gaseous sulfur dioxide under reduced pressure. 94 parts of a fraction distilled out at a temperature of 65° to 66° C. under a pressure of 6 mmHg was obtained. The fraction was colorless and clear. The infrared absorption spectrum of this fraction is the same as shown in the accompanying drawing. In view of the infrared absorption spectrum in combination with the result of the gas chromatography analysis, the fraction was confirmed to be ethyl-α-cyanoacrylate.

The purified monomer was of high purity and suitable as a base material for instantaneous adhesives.

EXAMPLE 10

100 parts of water and 150 parts of toluene were charged into a reaction vessel. 4 parts of $Ba(OH)_2$, 0.5 part of KOH and tributylbenzyl ammonium bromide were then dissolved by stirring in the solvents contained in the vessel. 31 parts of paraformaldehyde was further added to the solution and, the resulting mixture was stirred and heated to a temperature of 30° C.

113 parts of ethyl cyanoacetate was added to the mixture over about 20 minutes while the mixture was stirred. After the addition operation, stirring was continued at room temperature for 30 minutes. Thereafter, the resulting mixture was heated to a temperature of 80° C., and the mixture was reacted at that temperature for 20 minutes. At the end of that time, heating was stopped, and the reaction mixture was cooled. Thereafter, the reaction mixture was allowed to stand thereby to separate it into an aqueous phase and a polymer-toluene phase. After the aqueous phase was removed, the polymer-toluene phase was distilled under atmospheric pressure to carry out azeotropic dehydration. Thereafter, the procedure described in Example 9 was followed. 113 parts of a crude monomer distilled out at a temperature of 170° to 210° C. under a reduced pressure of 6 mmHg was obtained in a yield of 89.8%.

100 parts of the crude monomer was treated in the same manner as described in Example 9. 93 parts of a fraction distilled out at a temperature of 65° to 66° C. under a pressure of 6 mmHg was obtained. Analysis of this fraction indicated that it was ethyl-α-cyanoacrylate.

EXAMPLE 11

150 parts of water and 150 parts of cyclohexane were charged into a reaction vessel. 5 parts of $K_2CO_3$, 0.8 part of KOH, and 3 parts of a nonionic surface active agent, polyethylene oxide nonyl phenol ether (n=10) (e.g. Noniolite PN 10, trade name, in Example 7) were added to the vessel, and the resulting mixture was stirred. Ethyl cyanoacetate was further added dropwise to the mixture over 20 minutes. The resulting mixture was stirred for 20 minutes and thereafter was heated to a temperature of 60° to 70° C. for 30 minutes thereby to complete the reaction of the mixture.

The reaction mixture was cooled and allowed to stand thereby to separate it into an aqueous phase and a polymer-cyclohexane phase. After the aqueous phase was removed, 10 ml of 1-N $H_2SO_4$ and 140 parts of water were added to the polymer-cyclohexane phase to wash the phase with water. The resulting aqueous phase was again removed. The resulting polymer was azeotropically distilled to remove the remaining water. After the dehydration operation, the remaining cyclohexane was distilled off under atmospheric pressure and reduced pressure. A substantially colorless, transparent, viscous, liquid polymer was obtained.

The polymer, to which 2.1 parts of $P_2O_5$ and 0.6 part of hydroquinone were added, was depolymerized in a stream of gaseous sulfur dioxide. 112 parts of a fraction distilled out at a temperature of 170° to 220° C. under a reduced pressure of 6 mmHg was obtained in a yield of 89.6%.

100 parts of the crude monomer was purified in the same manner as described in Example 9. 93 parts of a fraction distilled out at a temperature of 66° to 67° C. under a reduced pressure of 6 mmHg was obtained.

The fraction was colorless and transparent. Analysis of this fraction indicated that it was ethyl-α-cyanoacrylate.

EXAMPLE 12

5 parts of 18-crown-6, and a mixture of 30 parts of water, 5 parts of $K_2CO_3$ and 0.5 part of KOH were added to 220 parts of toluene, and the resulting mixture was stirred to form a solution. 31 parts of paraformaldehyde was then added to the solution, and the resulting mixture was stirred at a temperature of 25° C. for 30 minutes.

113 parts of ethyl cyanoacetate was added to the mixture over about 20 minutes while the mixture was stirred, and the reaction of the resulting mixture was continued for 30 minutes. Thereafter, the reaction was further continued at a temperature of 80° C. for 30 minutes. The reaction mixture was cooled and allowed to stand thereby to separate it into an aqueous phase and a polymer-toluene phase. After the aqueous phase was removed, the polymer-toluene phase was washed two times with portions of 300 parts of water.

The resulting toluene solution was azeotropically distilled to remove the remaining water. Upon completion of the dehydration operation, the remaining toluene was distilled off under atmospheric pressure and reduced pressure. As a result, a polymer was obtained. This polymer was added to 1,000 parts of ethyl ether, and the mixture was stirred to wash the polymer. The polymer was then separated from the solvent. The separated polymer was treated under reduced pressure thereby to obtain 103 parts of a polymer. The polymer, to which 1.5 parts of $P_2O_5$ and 0.4 part of hydroquinone were added, was depolymerized in a stream of gaseous sulfur dioxide under a reduced pressure of 4 mmHg. 97 parts of a crude monomer distilled out at a liquid temperature of 165° to 200° C. was obtained in a yield of 94%.

The crude monomer, to which 0.8 part of $P_2O_5$ and 0.3 part of hydroquinone were added, was distilled in a stream of gaseous sulfur dioxide under reduced pressure. 75 parts of a fraction distilled out at a temperature of 65° to 66° C. under a reduced pressure of 6 mmHg was obtained. Analysis of this fraction indicated that it was ethyl-α-cyanoacrylate.

EXAMPLE 13

4 parts of polyethylene oxide nonylphenol ether (n=10) was added to 250 parts of water, and the resulting mixture was stirred. 8 parts of $K_2CO_3$ was dissolved in the above mixture, then 31 parts of paraformaldehyde was added thereto.

113 parts of ethyl cyanoacetate was added dropwise to the above-prepared solution over 20 minutes, and the resulting mixture was stirred for 30 minutes. Thereafter, the mixture was stirred at a temperature of 70° to 80° C. for 30 minutes to cause reaction thereof.

The reaction solution was cooled to room temperature and allowed to stand thereby to separate it into an aqueous phase and a polymer phase. After the aqueous phase was removed, 150 parts of toluene was added to the polymer phase. The resulting mixture was subjected to an azeotropic dehydration operation. Then, the same procedure as that described in Example 12 was followed thereby to obtain 113 parts of a fraction.

100 parts of the fraction was purified in the same manner as descibed in Example 12. As a result, 92 parts of colorless and a clear ethyl-α-cyanoacrylate was obtained.

What we claim is:

1. In a process for preparing an α-cyanoacrylate of the formula

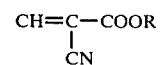

wherein R is selected from the group consisting of alkyl of 1 to 10 carbon atoms, substituted alkyl wherein said substituent is lower alkoxy, halogen or phenyl; cyclohexyl; phenyl or substituted phenyl wherein said substituent is halogen, which comprises reacting the corresponding cyanoacetate of the formula

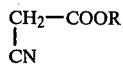

wherein R is as defined above, with formaldehyde at a molar ratio of about 1:1, in a solvent in the presence of a catalyst, wherein the improvement resides in said solvent being a mixture of water and an organic solvent which is immiscible with water and nonreactive to an alkaline substance, and said catalyst is a combination of (1) a first compound selected from the group consisting of onium compounds, macrocylic polyethers, and nonionic surface active agents, and (2) a second compound selected from the group consisting of alkali metal hydroxides, alkali metal carbonates, alkaline earth metal hydroxides, alkaline earth metal carbonates, and mixtures thereof.

2. A process as claimed in claim 1, in which the catalyst comprises a compound obtained by reacting (1) a first compound selected from the group consisting of onium compounds, macrocyclic polyethers, and nonionic surface active agents, and (2) a second compound selected from the group consisting of alkali metal hydroxides, alkali metal carbonates, alkaline earth metal hydroxides, alkaline earth metal carbonates, and mixtures thereof.

3. A process as claimed in claim 1, in which the formaldehyde is used by means of paraformaldehyde or formalin.

4. A process as claimed in claim 1 or 2, wherein the onium compound is a quaternary onium compound of the formula

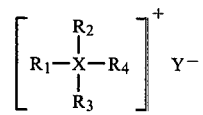

wherein X represents a nitrogen or phosphorous atom, each $R_1$, $R_2$, $R_3$, and $R_4$ represents independently a hydrocarbon radical selected from the group consisting of benzyl and alkyl having 1 to 22 carbon atoms, and $Y^-$ represents a monovalent anion selected from the group consisting of chloride, bromide, iodide, hydrogen sulfate, methyl sulfate, and ethyl sulfate.

5. A process as claimed in claim 1 or 2, wherein the macrocyclic polyether is selected from the group consisting of 1, 4, 7, 10, 13, 16-hexaoxacyclooctadecane and 3,4-benzo-1, 6, 9, 12, 15, 18, 21-heptaoxacyclotricos-3-ene.

6. A process as claimed in claim 1 or 2, wherein the nonionic surface active agent is a polyalkylene oxide ether wherein the alkylene oxide is 1 to 50 units and the ether group has about 8 to 20 carbon atoms.

7. A process as claimed in claim 1 or 2, wherein the onium compound is a sulfonium compound represented by the formula

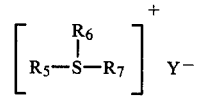

wherein each of $R_5$, $R_6$, and $R_7$ represents independently an alkyl having 1 to 18 carbon atoms, and $Y^-$ represents a monovalent anion selected from the group consisting of chloride, bromide, iodide, methyl sulfate, and ethyl sulfate.

8. A process as claimed in claim 1, carried out at a temperature ranging from room temperature to 85° C.

* * * * *